(12) United States Patent
Lunn

(10) Patent No.: US 6,513,254 B1
(45) Date of Patent: Feb. 4, 2003

(54) GUTTA PERCHA CONE GAUGE

(76) Inventor: Andrew R. Lunn, 5323 Brainerd Rd., Suite 106, Chattanooga, TN (US) 37411

(*) Notice: Subject to any disclaimer, the term of this patent is extended or adjusted under 35 U.S.C. 154(b) by 0 days.

(21) Appl. No.: 09/615,469

(22) Filed: Jul. 13, 2000

(51) Int. Cl.[7] .............................................. A61C 19/04
(52) U.S. Cl. ............................ 33/513; 33/511; 33/531; 33/555.3; 433/224
(58) Field of Search ......................... 33/513, 514, 511, 33/512, 531, 532, 562, 555.1, 555.3; 433/224

(56) References Cited

U.S. PATENT DOCUMENTS

| | | | | |
|---|---|---|---|---|
| 363,331 | A | * 5/1887 | Hammer | 33/169 |
| 1,027,287 | A | * 5/1912 | Shee | 33/169 |
| 1,389,486 | A | * 8/1921 | Brewer | 33/562 |
| 1,424,082 | A | * 7/1922 | Clopton | 33/514.1 |
| 2,650,435 | A | * 9/1953 | Kidd | 33/169 |
| 2,677,892 | A | * 5/1954 | Schecter | 33/562 |
| 3,358,826 | A | * 12/1967 | Siegel | 206/63.5 |
| 3,772,791 | A | * 11/1973 | Malmin | 32/57 |
| 3,911,587 | A | * 10/1975 | Forrest et al. | 33/174 R |
| 4,256,457 | A | * 3/1981 | Behring | 433/77 |
| 4,265,619 | A | * 5/1981 | Lucki et al. | 433/74 |
| 4,505,675 | A | * 3/1985 | Albert | 433/72 |
| 4,997,368 | A | * 3/1991 | Mayer et al. | 33/514 |
| 5,170,570 | A | * 12/1992 | Mays, Jr. | 33/512 |
| 5,685,085 | A | * 11/1997 | Bond | 33/555.3 |

FOREIGN PATENT DOCUMENTS

JP 308651 * 7/2000 ............... 433/224

OTHER PUBLICATIONS

Engineer–In–Training Preference Manual, 8th Edition, (p. 7-4, 7-5).*

* cited by examiner

Primary Examiner—Diego Gutierrez
Assistant Examiner—Madeline Gonzalez
(74) Attorney, Agent, or Firm—Alan Ruderman; Stephen J. Stark; Miller & Martin LLP

(57) ABSTRACT

A gauge for use in measuring, or evaluating, conical root canal gutta percha inserts has a body and a plurality of measuring locations. The measuring locations include a chute having first and second ends bounded by first and second walls and a floor. The first and second walls are portions of planes which meet at a first angle and a first distance between the first and second walls at the first end is greater than a second distance between the first and second walls at the second end. A standardized gutta percha cone may be received in the measuring location by placing the gutta percha cone in the chute and pushing it toward the second end to evaluate the taper and apex diameter of the gutta percha cone.

16 Claims, 2 Drawing Sheets

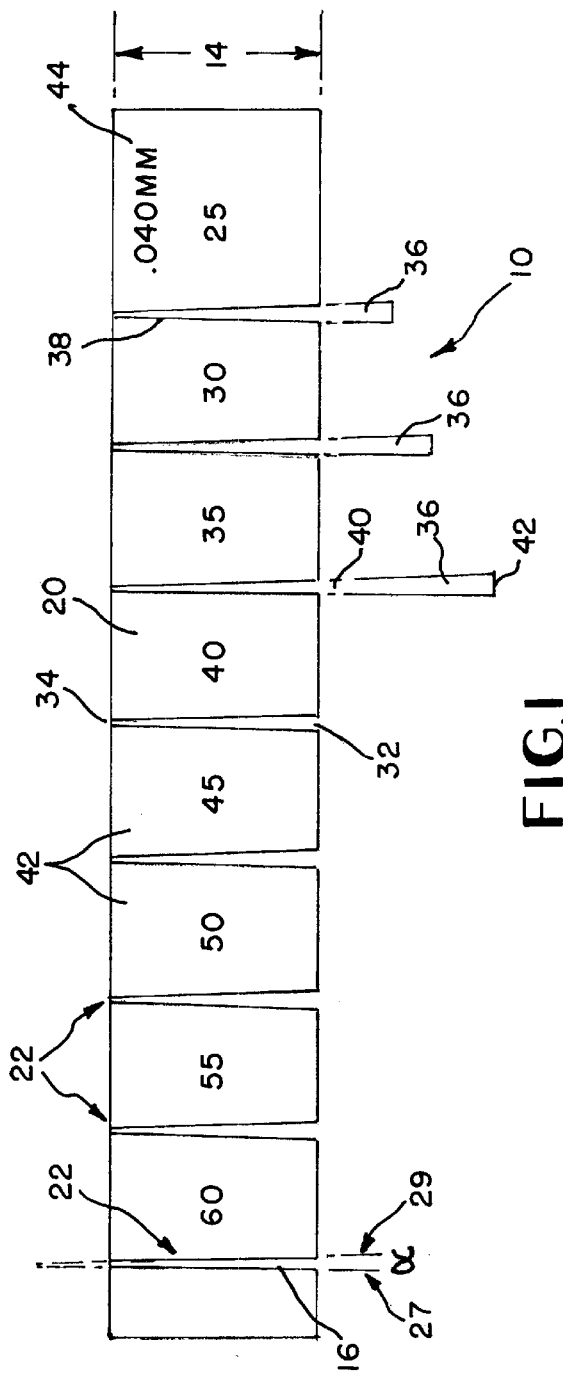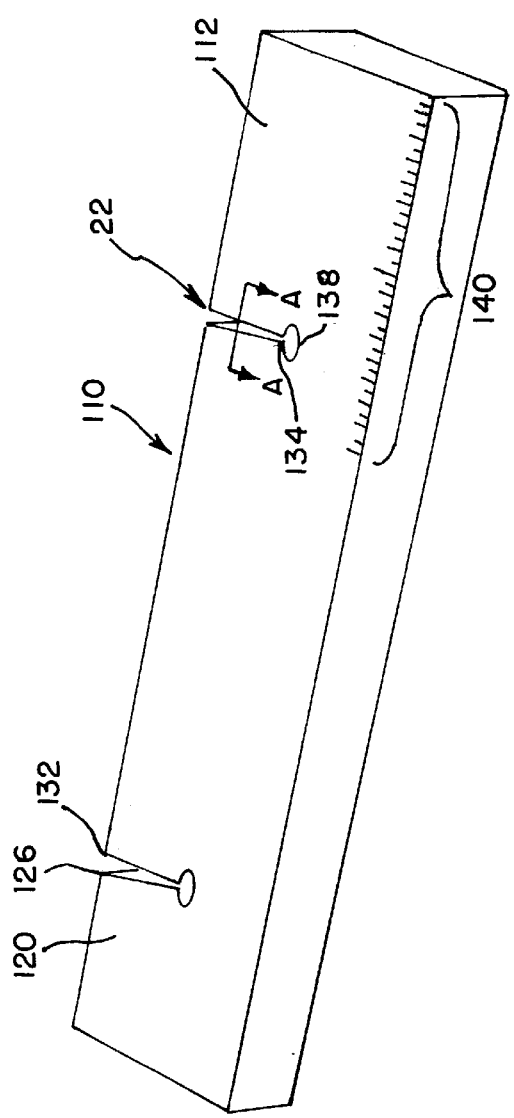

GUTTA PERCHA CONE GAUGE

BACKGROUND OF THE INVENTION

1. Field of the Invention

The present invention relates generally to devices utilized to measure the taper and diameter of conical inserts utilized in root canal procedures, and more specifically to a gauge capable of measuring and providing a specific sized gutta percha cone for use in a tooth during a root canal procedure.

2. Description of Related Art

Teeth have an outer layer of enamel surrounding the dentin. Within the dentin is a soft tissue, commonly referred to as pulp. The pulp is where the nerves, veins, arteries, and lymph vessels are located. Pulp is typically configured in a top pulp chamber which branches down to one, two and sometimes, even up to four root canals.

If the pulp is infected, the person will likely experience pain. Many times, the most logical choice of treatments is to have a root canal procedure performed. A number of different procedures are currently practiced for performing root canals. After applying a local anesthetic to numb the area of the infected tooth, a hole is drilled into the pulp chamber. The pulp chamber and root canal(s) are then cleaned of diseased pulp. Each root canal may be filed to a specific shape to allow for a secure fit with an inserted gutta percha point, or cone. Next, medication such as antibiotics may be inserted to fight bacteria. At this point, the crown of the tooth may be temporarily resealed, left open to drain, or the canals may be filled immediately depending on the particular procedure utilized.

Regardless of the particular procedure utilized, the canals are eventually filled. Typically, gutta percha in a substantially conical shape is inserted into the canal. A sealer is used with the gutta percha to assist in providing a secure fit within the tooth and preventing recontamination. The ability to accurately and consistently fit gutta percha cones into the shape of prepared root canals is critical in most obturation or root canal techniques.

There are two types of gutta percha cones available: standardized and non-standardized gutta percha cones. Standardized cones are conical in shape and extend from a small diameter tip or apex to a larger diameter base. The cones are tapered from the apex to the base at a specific taper. When a root canal has been filed with a specific file to a known shape, the endodonist, or dentist, may utilize a specific standardized shaped cone for obturating the canal.

Non-standardized cones are also tapered, but normally, not to the tolerances or degree of the standardized cones. They are marketed as fine, medium-fine, fine-medium, medium, large, extra-large, etc. The non-standardized cones are often heated and pressed into the root canal during the obturation process. Accordingly, capillaries, or other imperfections and passages, along the roots of the tooth can be filled with gutta percha.

A number of companies manufacture gutta percha cones. Some of the cones are hand rolled. Some of the cones are machine rolled. The tolerances for standardized cones under ISO standards are +/−0.05 mm which would correspond to +/−2.5 mm in a 0.02 mm taper, i.e., 0.02 mm per running millimeter of length. The tolerances for the files are held to a higher ISO standard of +/−0.02 mm. Therefore, a gutta percha cone selected from a manufacture, may not provide the fit desired by the practitioner and when placed within the canal may be short of the apex or out of the apex by up to 2.5 mm.

One gauge for gutta percha cones or points available on the market is made by a Swiss company, Maillefer. This device has a series of calibrated holes extending completely through the width of a plank member. The diameter of each hole is constant throughout the width of the gauge and is printed below each opening. Although this gauge measures diameter, it does not measure taper. Accordingly, even though the apex or base of a cone may be correctly sized, the taper may not provide the desired fit within a filed canal. For instance, if the taper is too large at a specific location along the cone, the cone may bind within the canal at that location preventing proper insertion of the cone. Additionally, if the taper is too small at a specific location along the cone, the cone may be loose within the cavity, possibly providing a location for bacteria growth.

SUMMARY OF THE INVENTION

It is an object of the present invention to provide a gauge to check the taper of a standardized gutta percha cone.

It is another object of the present invention to provide a gauge which allows a practitioner to modify a gutta percha cone by adjusting the apex point.

It is another object of the present invention to provide a gauge which checks the diameter of a standardized gutta percha cone at the apex and a plurality of locations along the length of the gutta percha cone between the apex and the base of the cone.

Yet another object of the present invention is to provide a gauge which may be utilized to check the diameter of the apex of a non-standardized gutta percha cone.

It is still a further object of the present invention to provide a gauge which assists in providing close tolerances between a gutta percha cone and a filed root canal.

Accordingly, the present invention recognizes and addresses the foregoing disadvantages, and others, of prior art construction and methods by providing a gutta percha cone gauge which measures, or checks, the diameter and taper of standardized gutta percha cones. The gauge may also be utilized to check certain diameters, such as the apex diameter, of non-standardized gutta percha cones.

The gauge includes a body with at least one measuring location. The measuring location includes a chute having first and second ends bounded by opposing angled walls. The preferred chute also includes a floor which supports a gutta percha cone during the measuring process. The first end of the chute has a larger cross section than the second end, and the second end is of a known width. The taper between the first and second end is a predetermined value. Additionally, the preferred gauge includes a plurality of measuring locations which correspond to a variety of apex diameters and/or tapers.

In order to check the specifications of a particular gutta percha cone with a gauge of the preferred embodiment, the cone is placed in the chute on the floor and pushed toward the second end of the chute. If the cone substantially touches the walls the length of the chute, then the taper over that length is correct. If the cone does not correspond with the angled walls along the taper, then the cone does not meet the tolerances of the gauge for that taper of cone. If the diameter of the apex of the cone corresponds with the diameter of the second end of the chute, then the cone was manufactured to be the correct diameter at its apex. If the cone corresponds in taper, but extends beyond the second end of the chute, the cone may be cut off with a scalpel or other sharp instrument to possibly provide an apex with the proper diameter.

BRIEF DESCRIPTION OF THE DRAWINGS

The particular features and advantages of the invention as well as other objects will become apparent from the following description taken in connection with the accompanying drawings in which:

FIG. 1 is a top plan view of the preferred embodiment of a gutta percha cone gauge constructed in accordance with the principles of the present invention;

FIG. 4 is a perspective view of an alternatively preferred embodiment of a gutta percha cone gauge according to the present invention.

DETAILED DESCRIPTION OF THE PREFERRED EMBODIMENT

Figure 2:
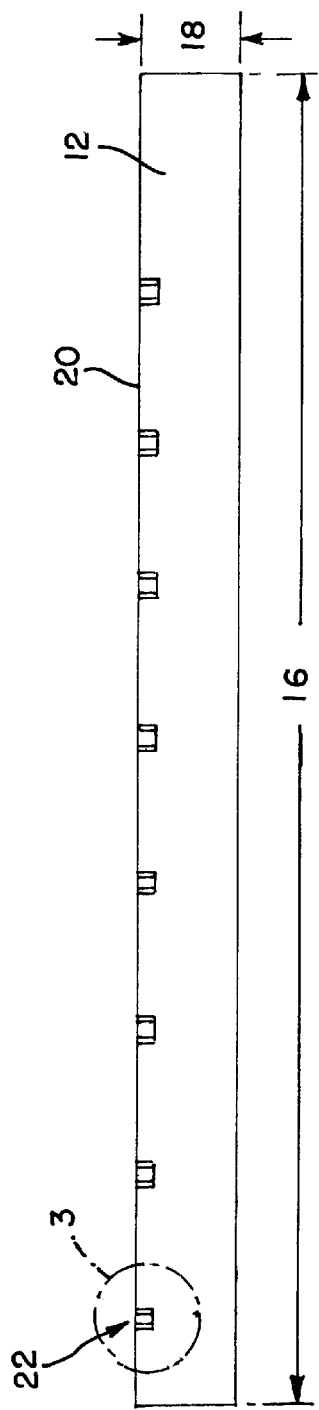
FIG. 2 is a side plan view of the gutta percha cone gauge of FIG. 1.
Figure 3:
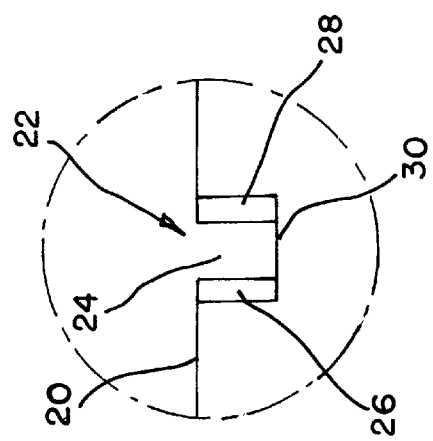
FIG. 3 is a side plan view of a measuring location of FIG. 2 shown in detail and greatly enlarged.

Accordingly, FIGS. 1–3 show a gutta percha cone gauge of the preferred embodiment, the gauge 10 including a body 12 having a length 14, a width 16 and a height 18. The body 12 may be constructed from metal bar stock, plastic or any other suitable material.

The body 12 has a first surface 20 which includes at least one measuring location generally shown at 22. The measuring location 22 has a channel or chute 24 defined by first and second walls 26,28 located above a floor 30 in the valley of the chute, as illustrated in FIG. 3. The chute 24 also has first and second ends 32,34 illustrated in FIG. 1.

The first and second walls 26,28 are angled relative to one another along the length 14 of the chute 24. Accordingly, the distance between the first and second walls 26,28 changes along the length 14. At the first end 32 of the chute 24, the first and second walls 26,28 are further apart than at the second end 34 of the chute 24. The change in distance between the first and second walls 26,28 along the length is intended to correspond with the taper of a correctly manufactured standardized gutta percha cone 36.

In the preferred embodiment, a linear relationship exists between the first and second ends 32,34 of the chute 24 and the separation distance of the first and second walls 26,28. The separation distance at an intermediate location could be calculated using an equation similar to $y=mx+b$ where b is the separation distance at the second end 34, m is the taper of the gutta percha cone 36 to be measured by the particular measuring location 22, x is the distance along the chute 24 from the second end 34, and finally, y is the separation distance between the first and second walls 26,28 at the location along the chute 24.

The first and second walls 26,28 are illustrated as planar members which would be portions of first and second planes 27,29 as shown in FIG. 1. The first and second planes 27,29 are angled relative to one another at a first angle, $\alpha$. For most applications, the first angle $\alpha$ will be between about 1.2 and about 7 degrees. However for some larger taper values, the first angle could be 50 degrees or more.

Standardized gutta percha cones 36 are manufactured to have a specific diameter at the apex 40 and a taper along the length of the gutta percha cone 36 from the apex 40 towards the base 42. The taper corresponds to the change in diameter per running unit of distance. Gutta percha cones 36 having apexes 40 on the order of 0.15 mm to 1.20 mm are presently available on the market in increments of 0.05 mm. Tapers may range from about 0.02 mm/mm to about 1.2 mm/mm, and are generally available in 0.02 mm increments therebetween.

As illustrated in FIG. 1, a dental practitioner or endodontist may insert a gutta percha cone 36 into the chute 22 at a measuring location 22. The gutta percha cone 36 is placed in the first end of the chute 24 and directed towards the second end 34 of the chute 24. A properly manufactured standardized gutta percha cone 36 substantially corresponds with the first and second walls 26,28 when properly placed in the correct measuring location 22 for that size gutta percha cone 36. A correctly positioned, and correctly manufactured, gutta percha cone 36 is illustrated in the first position 38 in FIG. 1.

If the standardized gutta percha cone 36 were not manufactured correctly, the practitioner would observe imperfections in the gutta percha cone 36 upon insertion of the gutta percha cone 36 into the measuring location 22. For instance, if the apex 40, or point of the gutta percha cone 36 is not the appropriate diameter, it could extend beyond the second end 34 of the chute 24 (if the apex diameter is too small), be spaced apart from one or both the first and second walls 26,28 at the second end 34 of the chute 24 (if the apex diameter is too small), or fail to reach the second end 34 of the chute 24 (if the apex diameter is too large). The floor 30 of the chute 24 may be a different color than the gutta percha cone 36 to facilitate identifying an imperfect gutta percha cone 36.

If the taper of the gutta percha cone 36 is imperfect, indications may be observed by the practitioner using the gauge 10. First, if the diameter of the gutta percha cone 36 is too large at a given location along the taper, the gutta percha cone 36 will bind at that location, and the apex 40 would likely fail reach the second end 34 of the chute 24. If the diameter of the gutta percha cone 36 is too small at a given location along the taper, the gutta percha cone 36 will be spaced apart from one or both of the first and second walls 26,28 at that location.

If a gutta perch cone 36 extends beyond the second end 34 of the chute 16, but is otherwise acceptable, the practitioner may use an instrument such as a scalpel to trim the apex 40 to be the appropriate diameter by cutting off the excess beyond the second end 34. Furthermore, non-standardized gutta percha cones (not shown) may be inserted into the second end 34 of the chute 24 toward the first end to determine if the apex diameter is correct. Thus, since the diameter is incorrect, the non-standardized gutta percha cone will be trimmed to have the correct apex diameter.

FIG. 1 also shows a plurality of reference cone identifiers 42 so that a user of the gauge will know which measuring location 22 corresponds to a particular standardized gutta percha cone 36. In the preferred embodiment, the reference cone identifiers 42 correspond to the apex diameter represented in thousandths of a millimeter, e.g. the identifiers illustrated being 25 to 60. Additionally, the preferred embodiment includes a second identifier 44, e.g. 0.04 mm, which indicates the taper of the standardized gutta percha cones 36 measured by the gauge 10.

An alternative embodiment of the gauge invention is illustrated as gauge 110 in FIG. 4. The alternative embodiment includes body 112 with measuring locations 122. Once again, the measuring locations 122 extend from a first end 132 to a second end 134 of a chute 124 bounded by first and second walls 126, 128 and floor 130. FIG. 3 would be an accurate cross section taken along the line A—A of FIG. 4. Referring back to FIG. 4, slot 138 is located at the second end 134 of the chute 124. The slot 138 preferably includes a slot floor similar to floor 30 of a different color than the gutta percha cone 36 to assist in determining if a gutta percha cone 36 extends into the slot 138. An additional feature of the alternatively preferred embodiment is scale

140 which allows the practitioner to measure lengths of gutta percha cones 36.

Numerous alternations of the structure herein disclosed will suggest themselves to those skilled in the art for a variety of applications, including those described above. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A gutta percha cone gauge comprising:

a body having a length and a measuring location channeled into an exterior surface of the body, said measuring location having a chute defined by first and second planar walls and a floor spaced from the exterior surface of the body, said chute having a first end extending the length of the body to a second end, the first and second walls spaced apart a first distance at the first end of the chute and a second distance at the second end of the chute, the first distance greater than the second distance, the first and second walls forming portions of first and second planes, and said first and second planes forming a first angle therebetween.

2. The gutta percha cone gauge of claim 1 further comprising a plurality of measuring locations including first and second measuring locations, the second distance of the first measuring location greater than the second distance of the second measuring location, and the chute of the first measuring location non-colinear with the chute of the second measuring location.

3. The gutta percha cone gauge of claim 1 wherein the chute of the measuring location is formed in the body and said second measuring location is parallel to the first measuring location.

4. The gutta percha cone gauge of claim 1 further comprising a reference cone identifier associated with the measuring location.

5. The gutta percha cone gauge of claim 4 further comprising a second identifier associated with the gauge.

6. A conical gutta percha root canal insert gauge comprising:

a body having a length and a measuring location configured to receive a conical gutta percha root canal insert, said measuring location having an exposed chute defined by first and second planar walls, said chute having a first end and extending the length of the body to a second end; the first and second walls spaced apart a first distance at the first end of the chute and a second distance at the second end of the chute, and the first spaced apart distance greater than the second spaced apart distance.

7. The gauge of claim 6 wherein the chute comprises a planar floor intermediate the first and second walls and said planar walls are perpendicular to said planar floor.

8. The insert gauge of claim 6 wherein the first and second walls form portions of first and second planes, and said first and second planes intersect at a first angle.

9. The insert gauge of claim 8 wherein the first angle is between about 1 and about 8 degrees.

10. The insert gauge of claim 8 wherein the first angle is less than about 55 degrees.

11. The conical root canal insert gauge of claim 6 further comprising a plurality of measuring locations including first and second measuring locations, the second distance of the first measuring location greater than the second distance of the second measuring location.

12. A gutta percha cone gauge comprising:

a body having a length and a measuring location adapted to evaluate the gutta percha cone, said measuring location defined by a channel in an exterior surface of the body extending a length between first and second ends, said length of the channel extending across the length of the body, said channel defined by first and second walls, the first and second walls spaced apart a first distance at the first end of the channel a second distance at the second end of the channel and a mathematical relationship existing along the length of channel to provide a third distance between the first and second walls along the length of the channel intermediate the first and second ends of the channel, said third distance greater than said second distance and less than said first distance.

13. The gutta percha cone gauge of claim 12 wherein the mathematical relationship further comprises a linear relationship.

14. The gutta percha cone gauge of claim 12 wherein first and second walls form portions of first and second planes, and said first and second planes intersect at a first angle.

15. The gutta percha cone gauge of claim 12 further comprising a floor between the first and second walls.

16. The gutta percha cone gauge of claim 12 further comprising a plurality of measuring locations including first and second measuring locations, the second distance of the first measuring location greater than the second distance of the second measuring location.

* * * * *